US006352965B1

(12) United States Patent
Saito et al.

(10) Patent No.: US 6,352,965 B1
(45) Date of Patent: Mar. 5, 2002

(54) TRANSPARENT SOLID DETERGENT COMPOSITION

(75) Inventors: Yoshinobu Saito; Nobuyuki Kishi; Tetsuo Nishina, all of Osaka (JP)

(73) Assignees: Shiseido Co., Ltd., Tokyo; Shiseido Honey-Cake Industry Co., Ltd., Osaka, both of (JP)

( * ) Notice: Subject to any disclaimer, the term of this patent is extended or adjusted under 35 U.S.C. 154(b) by 0 days.

(21) Appl. No.: 09/659,059

(22) Filed: Sep. 11, 2000

(51) Int. Cl.[7] .................................................. A61K 7/50
(52) U.S. Cl. ....................... 510/141; 510/151; 510/152; 510/155; 510/446; 510/499
(58) Field of Search ................................ 510/141, 151, 510/152, 446, 499

(56) References Cited

FOREIGN PATENT DOCUMENTS

| | | |
|---|---|---|
| WO | WO 95/03391 | 2/1995 |
| WO | 97/40131 | * 10/1997 |

OTHER PUBLICATIONS

Japanese Patent Office, "Patent Abstracts of Japan," Oct. 31, 1997, vol. 1997, No. 10, Publication No.: 09157690, Publication Date: Jun. 17, 1997, Application No.: 07289353, Application Date: Oct. 11, 1995.
Japanese Patent Office, "Patent Abstracts of Japan," Mar. 31, 1998, vol. 1998, No. 4, Publication No.: 09316486, Publication Date: Dec. 9, 1997, Application No. 08179992, Application Date: Jun. 20, 1996.
Japanese Patent Office, "Patent Abstracts of Japan," Oct. 31, 1997, vol. 1997, No. 10, Publication No.: 09157689, Publication Date: Jun. 17, 1997, Application No.: 07289354, Application Date: Oct. 11, 1995.
Japanese Patent Office, "Patent Abstracts of Japan", Publication No.: 54116006 A, Date of Publication: Sep. 10, 1979, Application No.: 53023992, Date of Filing: Mar. 2, 1978.
Japanese Patent Office, "Patent Abstracts of Japan", Publication No.: 04001297 A, Date of Publication: Jan. 6, 1992, Application No.: 01304280, Date of Filing: Nov. 21, 1989.
Japanese Patent Office, "Patent Abstracts of Japan", Publication No.: 09–157688, Date of Publication: Jun. 17, 1997, Application No.: 07–289352, Date of Filing: Oct. 11, 1995.
Japanese Patent Office, "Patent Abstracts of Japan", Publication No.: 09–157689, Date of Publication: Jun. 17, 1997, Application No.: 07–289354, Date of Filing: Oct. 11, 1995.
Japanese Patent Office, "Patent Abstracts of Japan", Publication No.: 09–157690, Date of Publication: Jun. 17, 1997, Application No.: 07–289353, Date of Filing: Oct. 11, 1995.

* cited by examiner

*Primary Examiner*—Necholus Ogden
(74) *Attorney, Agent, or Firm*—Snider & Associates; Ronald R. Snider

(57) ABSTRACT

A transparent solid detergent includes; 3.5 wt % or above of at least one fatty acid salt selected from the group consisting of compounds expressed by the following general formulas (I)–(III);

$$R—COO^{-}H_2N^{+}(CH_3)—CH_2–CH_2–SO_3^{-}X^{+} \quad (I)$$

$$R—COO^{-}H_2\ N^{+}—C_2—CH_2—SO_3^{-}X^{+} \quad (II)$$

$$R—COO^{-}H_2\ N^{+}—CH_2—CH_2—SO_2^{-}X^{+} \quad (III)$$

(wherein the formulas R is a saturated or unsaturated hydrocarbon group with carbon number 7~23, and X is an alkali metal or organic alkali)

sodium salt of fatty acid and/or potassium salt of fatty acid;

humectant; and water.

6 Claims, 1 Drawing Sheet

TRANSPARENT SOLID DETERGENT COMPOSITION

TECHNICAL FIELD

The present invention relates to a transparent solid detergent composition, and more particularly, to an improvement of counter ions of fatty acid thereof.

BACKGROUND ART

A transparent solid detergent composition has a high-class image from the transparency and also, in case where proper quantity of dye or pigment is added, it is widely used for high-class detergent for face etc. because of its deep color tone or metallic impression.

In prior arts, the transparent solid detergent composition includes a base materials such as fatty acid soap and transparent ingredients such as glycerol sugar etc..

As for the fatty acid soap, alkali metal soaps which have sodium ion or potassium ion etc. as "counter ions" of fatty acid are known.

These fatty acid alkali metal soaps have advantages such as low cost, good foaming and creamy feeling, but also have disadvantages such as slightly large frictional solubility and a feeling of tautness after face washing. When a soap of fatty acid and weak base such as triethanolamine and lysine etc. was used, a feeling of tautness after washing was found, and no sufficient improvement was achieved.

DISCLOSURE OF INVENTION

An object of the invention is to provide a transparent solid detergent composition having improved feeling of use and resistance to frictional solubility etc.

It has been found that a transparent solid detergent composition including fatty acid soap of N-methyltaurine alkali metal salt, taurine alkali metal salt or hypotaurine alkali metal salt can improve the frictional solubility and the feeling of tautness after washing without negative influence to its transparency.

Namely, the transparent solid detergent composition according to the present invention includes; 3.5 wt % or more of at least one fatty acid salt selected from the group consisting of compounds expressed by the following general formulas (I)–(III);

$$R—COO^{-}H_2\ N^{+}(CH_3)—CH_2—CH_2—SO_3^{-}X^{+} \quad (I)$$

$$R—COO^{-}H_2\ N^{+}—CH_2—CH_2—SO_3^{-}X^{+} \quad (II)$$

$$R—COO^{-}H_2\ N^{+}—CH_2—CH_2—SO_2^{-}X^{+} \quad (III)$$

(wherein the formulas, R is a saturated or unsaturated hydrocarbon group with carbon numbers of 7~23, and X is an alkali metal or organic alkali)

sodium salt of fatty acid and/or potassium salt of fatty acid;

humectant; and water.

It is also preferable that mole ratio of "the counter ions" of fatty acid is in following range;

| | |
|---|---|
| "the counter ions" of general formulas (I)~(III): | 5~50 |
| sodium: | 40~95 |
| potassium: | 0~20. |

It is also preferable that the total amount of the fatty acid salt is in 35–55 wt %; humectant is in 15–35 wt %; and water is in 15–25 wt % respectively in the composition.

Also, it is preferable to include polyether humectant which has polyhydric alcohol with three or more hydroxyl groups, 2–100 moles of addition polymerized propylene oxide and not greater than 50 moles of addition polymerized ethylene oxide. The amount of polyether humectant is preferably 5~50 wt % to the total humectant.

Also, it is preferable that the detergent composition be prepared by heating and dissolving a mixture of the fatty acid salt, humectant and water, and pouring the mixture into a frame, cooling and solidifying.

Furthermore, "a transparent solid detergent composition" in the specification means a substantially transparent composition from which color agents such as dye, pigment are eliminated.

BEST MODE FOR CARRYING OUT THE INVENTION

Figure 1:
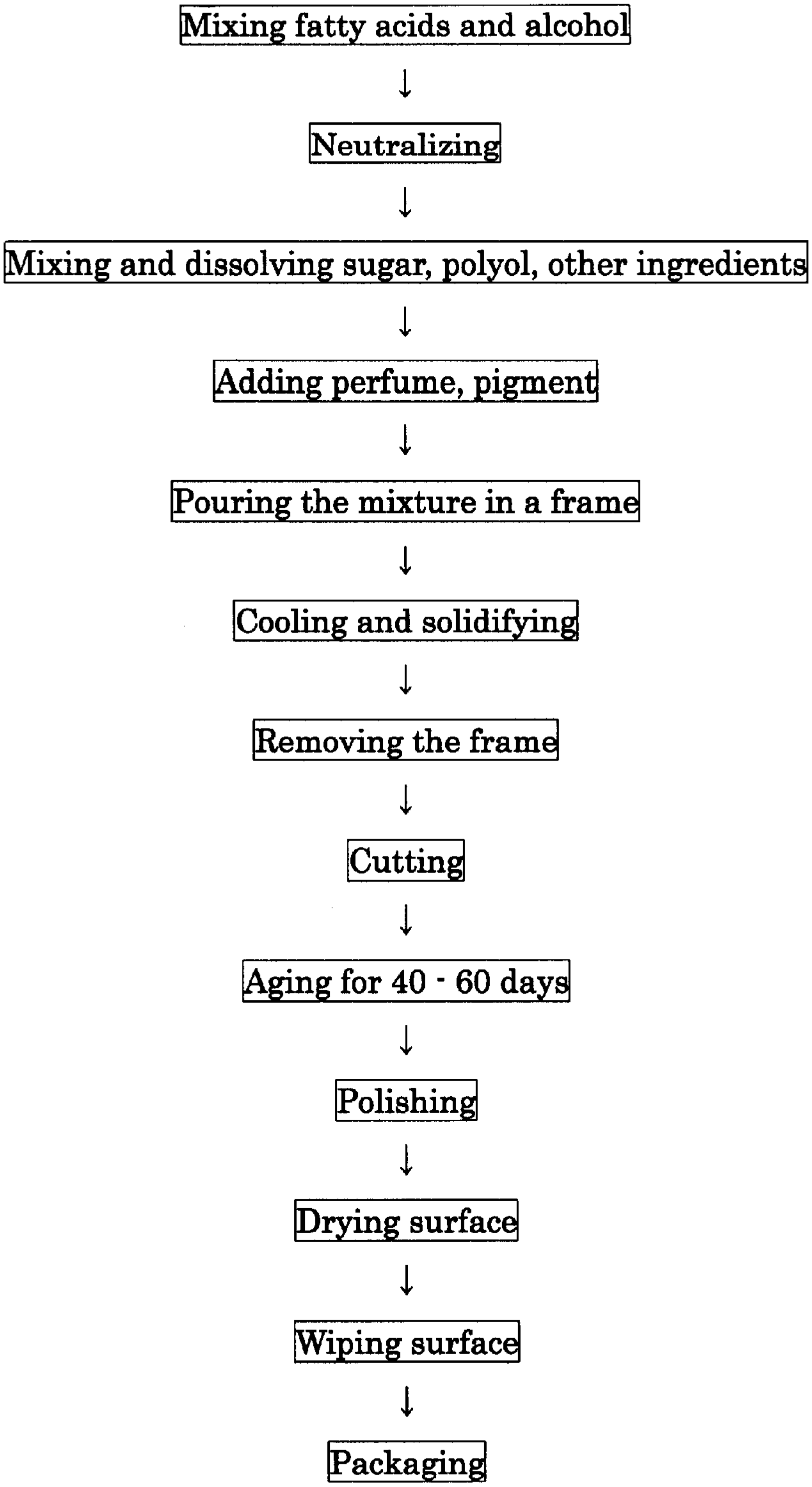
FIG. 1 is an explanatory view of suitable production process of the transparent solid detergent composition according to the present invention.

The preferred embodiments of the present invention will be explained below.

In this invention, R of the general formulas (I)~(III) is a saturated or unsaturated hydrocarbon group having a carbon number of 7~23. As for hydrocarbons used in the present invention, examples are as follows; a straight chain saturated hydrocarbon group such as a heptyl group, an octyl group, anonyl group, a decyl group, an undecyl group, a dodecyl group, a tridecyl group, a tetradecyl group, a pentadecyl group, a hexadecyl group, a heptadecyl group, an octadecyl group, a tetraeicocyl group; a branched chain saturated hydrocarbon group such as a 2-methyheptadecyl group, 2-ethylpentyl group; a straight chain unsaturated hydrocarbon group such as a 8-heptadecenyl group, oleil group, 4,6-octadecadienyl group; and a branched chain unsaturated hydrocarbon group such as a 2-methyloctadeca-6-enyl group.

As for X used in the above general formulas (I)–(III), examples are as follows; an alkali metal such as sodium, potassium and lithium; and an organic alkali such as triethanolamine, diethanolamine and lysine.

The R—COO— moiety of the fatty acid sodium salt or fatty acid potassium salt is the same as the definition of R—COO— of general formulas (I)~(III).

It is preferable that the fatty acid of the general formulas (I)~(III) and the fatty acid of the sodium salt and potassium salt be the same.

Further, it is preferable to prepare the detergent composition by adding an alkali agent comprising the taurine counter ion, sodium ion and potassium ion substantially equivalent to the fatty acid, which is heated and dissolved.

As for humectant used in the present invention, examples are as follows; saccharides or polyol such as sucrose, sorbitol, glycerol, 1,3-butyleneglycol, propyleneglycol, dipropyleneglycol. In these, polyether humectant which has polyhydric alcohol with three or more hydroxyl groups, 2–100 moles of addition polymerized propylene oxide and not greater 50 moles of addition polymerized ethylene oxide is especially preferable. The polyether humectant is preferably included 5~50 wt % to the total humectant. As for polyhydric alcohol, the following are exemplified; glycerol, diglycerin, pentaerythritol, and dipentaerythritol. Further, various monosaccharides, disaccharides, and oligosaccharides can be used for the polyhydric alcohol.

As for disaccharides used in the polyhydric alcohol of the polyether compound, examples are as follows; trehalose, saccharose, maltose, and lactose. As for polysaccharide, gentianose, raffinose, melezitose, stachyose, cellulose, hemicellulose, starch and chitin glycogen are exemplified. As for sugar alcohol, D-sorbitol, D-mannose and D-mannitol etc. are exemplified. As for sugar carboxylic acid, D-mannonic acid, D-gluconic acid, aldonic acid and uronic acid etc. are exemplified. As for carbohydrate derivative, examples are as follows; inositol, alpha-acrose, glucoson, methylfructopyranoside, sorbitan, ethylglucofuranoside, gluconolactone, arbutin, monoacetylsorbitol, diacetylsorbitan, sorbitan lauric acid ester, sorbitan oleic acid ester, and glucose phosphoric ester.

Also the transparent solid detergent composition according to the present invention can include the following agents in addition to the essential components. Examples are an anionic surface active agent such as soaps that are usually included in a detergent composition, alkyl sulfuric ester (salt), polyoxy ethylene alkyl ether sulfuric acid (salt), hydroxyalkyl ether carboxylic acid (salt), an ampholytic surface active agent such as an imidazoline ampholytic surface active agent and betaine ampholytic surface active agent etc; a nonionic surface active agent such as polyoxyethylene alkyl ether, polyoxyethylene fatty acid ester, sugar fatty acid ester, alkyl glycoside, and maltitol hydroxy aliphatic ether; a cationic surface active agent such as trimethylalkyl ammonium chloride etc; a plant extraction component such as swertia herb, peony root, iris, and horsetail; a drug such as tranexamic acid, and arbutin; perfume; and antiseptics.

The transparent solid detergent composition according to the present invention is preferably manufactured as shown in FIG. 1.

Namely, various kinds of fatty acid and a lower alcohol such as ethyl alcohol are heated and dissolved in at 40–60° C. Added to this are the alkalis that become to "counter ions" and neutralize. To this are added the humectant and other additives, such as the saccharides, polyol and the like. This mixture is dissolved homogeneously. If necessary, perfume and coloring agent are added. This solution is poured into a frame for cooling and solidifying. After cooling, the frame is removed. If necessary these are cut into a predetermined shape and allowed to age and dry for 40–60 days. If necessary, molding polishing, surface drying, wiping the surface and packing are performed.

Preferred embodiments of the present invention will be explained in detail hereunder.

Evaluation method

In the following test examples, evaluations were conducted as follows.

Solidification

| | |
|---|---|
| Good: | Solidification as a whole |
| Average (Av.): | Solidification as a whole but soft |
| Bad: | Solidification is not obtained |

Transparency

Each sample was cut to the thickness of 20 mm and placed on 26 points printed character and the readability thereof was determined and evaluated according to the following standards.

| | |
|---|---|
| Very good (V.G.): | Clearly readable |
| Good: | Readable |
| Average: | Read it with slight difficulty |
| Bad: | Unreadable |

Homogeneity

| | |
|---|---|
| Good: | Homogeneous as a whole |
| Average: | Partially homogeneous |
| Bad: | Crystallized as a whole |

Foaming

Twenty women panelists (20–40 years old) tested the sample of solid soaps in actual use of face washing, foaming the soaps by hand with tap water, and evaluated according to the following standards.

| | |
|---|---|
| Very good: | Extremely fine foaming |
| Good: | Fine foaming |
| Average: | Average foaming |
| Bad: | Bad foaming |

Feeling of Tautness After Washing

Twenty women panelists (20–40years old) tested the sample of solid soaps in actual use of face washing, foaming the soaps by hand with tap water, and evaluated according to the following standards.

| | |
|---|---|
| Very good: | No feeling of tautness after washing and extremely fine. |
| Good: | No feeling of tautness and fine |
| Average: | Average |
| Bad: | Feeling of tautness |

Frictional Solubility

Frictional solubility was evaluated according to the friction solubility of Japan Industrial Standard K-3304.

A sample fragment of predetermined weight (cross section 15 mm×20 mm) was placed on the film wetted with tap water of 40° C. This film was rotated and the soap was rubbed and dissolved for 10 minutes. The friction solubility of a certain area was evaluated from the weight before and after the friction dissolving.

| | |
|---|---|
| Very good: | 20 or less. |
| Good: | 20~35. |
| Average: | 35~50. |
| Bad: | 50 or more. |

Counter Ion of Fatty Acid

Transparent solid detergent compositions were prepared by using sodium, sotium N-methyltaurate, sodium N-taurate, and sodiium hypotaurate as the counter ions of mixed fatty acid and various tests were conducted. The results are shown in Table 1.

The salt of the mixed fatty acid (beef tallow fatty acid/coconut oil fatty acid=8/2) was mixed in the proportions of Table 1.

40 wt % of the fatty acid salt, 10 wt % of sorbitol, 5 wt % of glycerine, 10 wt % of sugar, 15 wt % of ethanol and 20% of ion-exchanged water were mixed and the detergent compositions were prepared by frame method.

The mixture was heated 70–80° C. and homogeneously dissolved, and the resultant was poured in a frame. After this process, the composition was cooled and solidified and aged to prepare a solid detergent composition.

The counter ions are added in the amount of equivalent to the fatty acid and shown in mole ratio unless otherwise stated.

TABLE 1

| | Test example | | | |
|---|---|---|---|---|
| | 1 | 2 | 3 | 4 |
| Sodium | 100 | 80 | 80 | 80 |
| Sodium N-methyltaurate | — | 20 | — | — |
| Sotium N-taurate | — | — | 20 | — |
| Sodium Hypotaurate | — | — | — | 20 |
| Solidification | Good | Good | Good | Good |
| Transparency | V.G | V.G | V.G | V.G |
| Homogeneity | Good | Good | Good | Good |
| Foaming | Av. | Good | Good | Good |
| Feeling of tautness | Bad | V.G. | V.G. | V.G |
| Feeling of solubility | Good | V.G. | V.G. | V.G |

As shown in Table 1, the detergent compositions including "the counter ions" of sodium N-methyltaurate sodium N-taurate, and sodium hypotaurate were clearly improved in foaming, feeling of tautness and frictional solubility etc. in comparison with the counter ion of sodium only even for same fatty acid.

Mole Ratio of Taurine Counter Ion

The inventors conducted tests to determine the suitable "counter ion ratio" (mole ratio) of sodium N-methyltaurate. The test method is the same as the example of Table 1.

TABLE 2

| Test example | 5 | 6 | 7 | 8 | 9 | 10 | 11 | 12 |
|---|---|---|---|---|---|---|---|---|
| Sodium | 99 | 95 | 90 | 80 | 70 | 60 | 50 | 40 |
| N-methyl-taurine Na | 1 | 5 | 10 | 20 | 30 | 40 | 50 | 60 |
| Solidification | Good | Good | Good | Good | Good | Good | Good | Good |
| Transparency | V.G | V.G | V.G | V.G | V.G | V.G. | Good | Av. |
| Homogeneity | Good | Good | Good | Good | Good | Good | Good | Bad |
| Foaming | Av. | Good | Good | Good | Good | Good | Good | — |
| Feeling of tautness | Bad | Good | Good | V.G. | V.G. | V.G. | V.G | — |
| Frictional solubility | Good | Good | Good | V.G. | V.G. | V.G. | V.G. | — |

As is clear from Table 2, the effect of N-methyltaurine can be observed from the mole ratio of from 5 or more. The effect of the sodium N-methyltaurate fatty acid is observed when it was 3.5 wt % or more of the composition.

Effect of Potassium Ion

Generally the addition of potassium ion has a tendency to promote a disadvantage in solidification, while improving detergency and foaming. Tests were conducted on the addition effect of the potassium ion with the various quantities of sodium N-methyltaurate The test method is the same as method of Table 1. Proportions of the counter ions were shown in mole ratio.

TABLE 3

| Test example | 13 | 14 | 15 | 16 | 17 | 18 | 19 | 20 |
|---|---|---|---|---|---|---|---|---|
| Sodium | 90 | 85 | 80 | 70 | 60 | 50 | 40 | 30 |
| Potassium | 10 | 10 | 10 | 10 | 10 | 10 | 10 | 10 |
| N-methyl-taurine Na | 0 | 5 | 10 | 20 | 30 | 40 | 50 | 60 |
| Solidification | Good | Good | Good | Good | Good | Good | Good | Bad |
| Transparency | V.G. | V.G. | V.G. | V.G. | V.G. | V.G. | Good | — |
| Homogeneity | Good | Good | Good | Good | Good | Good | Good | — |
| Foaming | Good | Good | Good | Good | Good | Good | Good | — |
| Feeling of tautness | Bad | Good | Good | V.G. | V.G. | V.G. | V.G. | — |
| Frictional solubility | Av. | Good | Good | V.G. | V.G. | V.G. | V.G. | — |

TABLE 4

| Test example | 21 | 22 | 23 | 24 | 25 | 26 | 27 |
|---|---|---|---|---|---|---|---|
| Sodium | 80 | 75 | 70 | 60 | 50 | 40 | 30 |
| Potassium | 20 | 20 | 20 | 20 | 20 | 20 | 20 |
| N-methyltaurine Na | 0 | 5 | 10 | 20 | 30 | 40 | 50 |
| Solidification | Good | Good | Good | Good | Good | Good | Bad |
| Transparency | V.G. | V.G. | V.G. | V.G. | V.G. | V.G. | — |
| Homogeneity | Good | Good | Good | Good | Good | Good | — |
| Foaming | V.G. | V.G. | V.G. | V.G. | V.G. | V.G. | — |
| Feeling of tautness | Bad | Good | Good | V.G. | V.G. | V.G. | — |
| Frictional solubility | Av. | Good | Good | V.G. | V.G. | Good | — |

TABLE 5

| Test example | 28 | 29 | 30 | 31 | 32 | 33 | 34 |
|---|---|---|---|---|---|---|---|
| Sodium | 70 | 60 | 50 | 40 | 60 | 50 | 40 |
| Potassium | 30 | 30 | 30 | 30 | 40 | 40 | 40 |
| N-methyltaurine Na | 0 | 10 | 20 | 30 | 0 | 10 | 20 |
| Solidification | Good | Good | Good | Bad | Good | Bad | Bad |
| Transparency | V.G. | Bad | Bad | Bad | Bad | Bad | Bad |
| Homogeneity | Good | Bad | Bad | Bad | Bad | Bad | Bad |
| Foaming | V.G. | — | — | — | — | — | — |
| Feeling of tautness | Bad | — | — | — | — | — | — |
| Frictional solubility | Bad | — | — | — | — | — | — |

As is clear from Tables 3 to 5, a 20 or less mole ratio of potassium ion improved forming ability. However, exceeding 20 mole ratio of potassium may have a negative effect on solidification and homogeneity.

Amount of Fatty Acid Salt

In next, the inventors conducted tests for the amount of fatty acid salt in the composition.

A fatty acid salt part and a remaining part were prepared as below and these were compounded and mixed with a proper ratio and the compositions for testing were obtained.

Fatty Acid Salt Part

Salts of mixed fatty acid (C14/C16/C18/isoC18=60/20/10/10) were blended so as to be a mole ratio of fatty acid sodium salt/fatty acid potassium salt/fatty acid sodium N-methyltaurate salt=70/10/20.

Remaining Part

The remaining part was prepared by blending 10 parts of sorbitol, 5 parts of glycerol, 10 parts of sugar, 15 parts of ethanol and 20 parts of ion exchanged water.

The mixture of the fatty acid salt part and the remaining part were heated 40–60° C. and homogeneously dissolved, and the resultant was poured in the frame. After this process, the composition was cooled and solidified and allowed to age to prepare a solid detergent composition.

TABLE 6

| Test example | 35 | 36 | 37 | 38 | 39 | 40 | 41 |
|---|---|---|---|---|---|---|---|
| Fatty acid salt part | 30 wt % | 35 | 40 | 45 | 50 | 55 | 60 |
| Solidification | Bad | Good | Good | Good | Good | Good | Good |
| Homogeneity | — | Good | Good | Good | Good | Good | Bad |

As a result of Table 6, the blending amount of the fatty acid salt in the composition was preferably 35–55 wt %.

Humectant Amount

A test method for the determination of preferable amount of humectant is as below. Ethanol was added to the mixed fatty acid (C14/C16/C18/isoC18=60/20/10/10) and heated it to about 60° C. in a reaction container. Sodium hydroxide/sodium N-methyltaurate with the proportion of the listed below was added to this and neutralized and obtained the fatty acid soap part. The fatty acid soap part and humectant were blended as listed below, and 10 wt % of ethanol and 20 wt % of ion exchanged water were added and heated 70~80° C. to dissolve. The detergent compositions were prepared by frame method. The results are shown in Tables 7–10.

TABLE 7

| | Test example | | | | |
|---|---|---|---|---|---|
| | 42 | 43 | 44 | 45 | 46 |
| Na/N-methyltaurine Na | | | 95/5 | | |
| Soap part | 25 | 35 | 45 | 55 | 60 |
| Total humectant amount | 45 | 35 | 25 | 15 | 10 |
| Solidification | Av. | Good | Good | Good | Impossible |
| Transparency | V.G. | V.G. | V.G. | V.G. | — |
| Homogeneity | Good | Good | Good | Good | — |
| Foaming | Good | Good | Good | Good | — |
| Feeling of tautness | Good | Good | Good | Good | — |
| Frictional solubility | Av. | Good | Good | Good | — |

TABLE 8

| | Test example | | | | |
|---|---|---|---|---|---|
| | 47 | 48 | 49 | 50 | 51 |
| Na/N-methyltaurine Na | | | 75/25 | | |
| Soap part | 25 | 35 | 45 | 55 | 60 |
| Total humectant amount | 45 | 35 | 25 | 15 | 10 |
| Solidification | Bad | Good | Good | Good | Good |
| Transparency | — | V.G. | V.G. | V.G. | Av. |
| Homogeneity | — | Good | Good | Good | Av. |
| Foaming | — | Good | Good | Good | Good |
| Feeling of tautness | — | V.G. | V.G. | Good | Good |
| Frictional solubility | — | Good | V.G. | V.G. | Good |

TABLE 9

| | Test example | | | | |
|---|---|---|---|---|---|
| | 52 | 53 | 54 | 55 | 56 |
| Na/N-methyltaurine Na | | | 50/50 | | |
| Soap part | 25 | 35 | 45 | 55 | 60 |
| Total humectant amount | 45 | 35 | 25 | 15 | 10 |
| Solidification | Bad | Good | Good | Good | Good |
| Transparency | — | V.G. | V.G. | Good | Av. |
| Homogeneity | — | Good | Good | Good | Av. |
| Foaming | — | Good | V.G. | V.G. | Good |
| Feeling of tautness | — | V.G. | V.G. | V.G. | Good |
| Frictional solubility | — | V.G. | V.G. | V.G. | V.G. |

TABLE 10

| | Test example | | | | |
|---|---|---|---|---|---|
| | 57 | 58 | 59 | 60 | 61 |
| Na/N-methyltaurine Na | | | 40/60 | | |
| Soap part | 25 | 35 | 45 | 55 | 60 |
| Total humectant amount | 45 | 35 | 25 | 15 | 10 |
| Solidification | Bad | Av. | Good | Good | Good |
| Transparency | — | Av. | Bad | Bad | Bad |
| Homogeneity | — | Av. | Bad | Bad | Bad |
| Foaming | — | Av. | Good | Good | Good |
| Feeling of tautness | — | V.G. | V.G. | V.G. | Good |
| Frictional solubility | — | Good | V.G. | V.G. | V.G. |

As is clear from Tables 7–10, transparency sometimes becomes a little low, when the proportion of N-methyltaurine increases in the counter ions. However, it is possible to improve the transparency by addition of proper amount of the humectant. Especially, when the blending amount of the humectant is 15–35 wt % in the composition, improvement of transparency,, feeling of tautness and solubility can be observed.

Effect of the Polyether Humectant

Ethanol was added to the mixed fatty acid (C14/C16/C18/isoC18=60/20/10/10) and heated to about 60 ° C. in a reaction container. Sodium hydroxide/potassium hydroxide/sodium N-methyltaurate with the proportion of 80/10/10 were added to this and neutralized and the fatty acid soap part was obtained. 40 wt % of the fatty acid soap part and 25% of humectant with the proportions (weight ratio) in Table 11 were blended, and 15 wt % of ethanol and 20 wt % of ion exchanged water were added and heated 40~60° C. to dissolve the mixture. The detergent compositions were prepared by frame method.

TABLE 11

| | Test example | | | |
|---|---|---|---|---|
| | 62 | 63 | 64 | 65 |
| Sorbitol | 40 | 40 | 40 | 40 |
| Glycerol | 20 | 15 | 10 | 0 |
| Sugar | 40 | 40 | 40 | 40 |
| POP (9) diglycerylether | 0 | 5 | 10 | 50 |
| Solidification | Good | Good | Good | Good |
| Homogeneity | Good | Good | Good | Good |
| Foaming | Good | Good | Good | Good |
| Feeling of tautness | Good. | V.G. | V.G. | V.G. |
| Frictional solubility | Good | V.G. | V.G. | V.G. |

As is clear from Table 11, the polyether humectant has a better feeling of tautness and solubility effect in comparison with other humectant components.

Counter Ions of the Formulas (I)–(III)

Ethanol was added to the mixed fatty acid (C14/C16/C18/isoC18=60/20/10/10) and heated to about 60° C. in a reaction container. Counter ions of sodium hydroxide/potassium hydroxide/counter ions in Table 12 with the proportions of 70/10/20 were added to this and neutralized and the fatty acid soap part was obtained. 40 wt % of the fatty acid soap part, 10 wt % of sorbitol, 5 wt % of glycerine, 10 wt % of Sugar, 15 wt % of ethanol and 20 wt % of ion exchanged water were added and heated 40~60° C. to dissolve the mixture. The detergent compositions were prepared by frame method.

TABLE 12

| Example | Ion | Solidification | Homogeneity | Foaming | Feeling | Solubility |
|---|---|---|---|---|---|---|
| 66 | N-methyltaurine Na | Good | Good | Good | V.G. | V.G. |
| 67 | N-methyltaurine K | Good | Good | Good | V.G. | V.G. |
| 68 | N-taurine Na | Good | Good | Good | V.G. | V.G. |
| 69 | N-taurine K | Good | Good | Good | V.G. | V.G. |
| 70 | N-hypotaurine Na | Good | Good | Good | V.G. | V.G. |
| 71 | N-hypotaurine K | Good | Good | Good | V.G. | V.G. |
| 72 | N-methyltaurine TEA | Good | Good | Good | V.G. | V.G. |

Because of the results of Table 12, counter ions of the present invention have not to be limited.

The preferred blending examples of the present invention will be explained hereinunder.

All of the blending examples were prepared by frame method and had excellent transparency, resistance to friction solubility and feel of use.

Blending Example I

| | |
|---|---|
| Lauric acid | 7.0 wt % |
| Myristic acid | 10.0 |
| Palmitic acid | 3.0 |
| Stearic acid | 6.0 |
| Iso stearic acid | 1.5 |
| Sorbitol | 7.5 |
| Alcohol | 15.0 |
| Salt of Edete acid | 0.1 |
| Sodium hydroxide | 1.1 |
| Sodium N-methyltaurate | 9.2 |
| Sodium hydroxyalkyl ether carboxylate | 3.0 |
| Salt | 0.5 |
| Sucrose | 10.0 |
| POP (9) diglyceryl ether | 5.0 |
| BHT | 0.1 |
| Coloring agent | q.s. |
| Ion exchanged water | Balance |

| | |
|---|---|
| Lauric acid | 5.0 wt % |
| Myristic acid | 10.0 |
| Palmitic acid | 3.0 |
| Stearic acid | 5.0 |
| Isostearic acid | 3.0 |
| Glycerol | 10.0 |
| Diglycerin | 3.5 |
| Sorbitol | 4.0 |
| Alcohol | 10.0 |
| Salt of edete acid | 0.1 |
| Sodium hydroxide | 3.6 |
| Sodium N-methyltaurate | 3.5 |
| Sodium hydroxyalkyl ether carboxylate | 2.0 |
| POE (60) hardening castor oil | 2.0 |
| Lauroyl imidazolinium betaine | 2.0 |
| Salt | 0.5 |
| Sucrose | 10.0 |
| BHT | 0.1 |
| Coloring agent | q.s. |
| Ion exchanged water | Balance |

| | |
|---|---|
| Lauric acid | 8.0 wt % |
| Myristic acid | 12.0 |
| Palmitic acid | 4.0 |
| Stearic acid | 6.0 |
| Oleic acid | 4.0 |
| Sorbitol | 11.0 |
| Glycerol | 5.0 |
| Alcohol | 16.5 |
| Salt of edete acid | 0.1 |
| Sodium hydroxide | 4.2 |
| Sodium N-methyltaurate | 5.5 |
| Salt | 0.5 |
| Sucrose | 11.0 |
| BHT | 0.1 |
| Titanium oxide | 0.1 |
| Coloring agent | q.s. |
| Ion exchanged water | Balance |

| | |
|---|---|
| Lauric acid | 7.0 wt % |
| Myristic acid | 10.0 |
| Palmitic acid | 3.0 |
| Stearic acid | 6.0 |
| Isostearic acid | 1.5 |
| Sorbitol | 7.5 |
| Alcohol | 15.0 |
| Salt of edete acid | 0.1 |
| Sodium hydroxide | 6.0 |
| Potassium N-taurate | 2.1 |
| Sodium hydroxyalkyl ether carboxylate | 3.0 |
| Salt | 0.5 |
| Sucrose | 10.0 |
| POP (9) diglyceryl ether | 0.1 |
| Coloring agent | q.s. |
| Ion exchanged water | Balance |

As described above, according to the transparent solid detergent composition of the present invention, it is possible to improve transparency, resistance to solubility, and feeling after washing by using the aforementioned counter ions of fatty acid.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A transparent solid detergent composition comprising;

(i) a mixture of fatty acid salts consisting of:

(a) 3.5 or more of weight % of at least one fatty acid salt expressed by the following general formula:

$$R—COO^-H_2N^+A^-X^+$$

wherein R is a saturated or unsaturated hydrocarbon group having 7 to 23 carbon atoms, $H_2N^+A^-X^+$ is a counter anion selected from the group consisting of:

$$H_2N^+(CH_3)—CH_2—CH_2—SO_3^-X^+;$$

$$H_2N^+—CH_2—CH_2—SO_3^-X^+; \text{ and}$$

$$H_2\ N^+—CH_2—CH_2—SO_2^-X^+$$

and X is an alkali metal or organic alkali; and (b) 35 to 55 weight % of sodium salt of fatty acid and/or potassium salt of fatty acid other than fatty acids recited under (a);

(ii) 15 to 35 weight % of a humectant; and (iii) 15 to 25 weight % of water.

2. A transparent solid detergent composition according to claim 1, wherein the counter ions of fatty acid are in a mole ratio of counter ions of the formula $H_2N^+A^-X^+$ to sodium ions to potassium ions of fatty acid of about 5–50:40–95:0–20 and wherein said sodium and potassium ions are sodium and potassium ions other than sodium and potassium ions present in the formula $H_2N^+A^-X^+$.

3. A transparent solid detergent composition according to claim 1, wherein the humectant comprises a polyether humectant comprising (i) a polyhydric alcohol having at least three hydroxyl groups and (ii) at least one addition-polymerized alkylene oxide selected from the group consisting of an addition-polymerized propylene oxide and an addition-polymerized ethylene oxide, an amount of the polyether humectant being from 5 to 50% by weight of a total amount of the humectant.

4. A transparent solid detergent composition according to claim 2, comprising, as a percent by weight of the total weight of the composition, 35–55 % of the total amount of the fatty acid salts, 15–35 % of the humectant, and 15–25 % of water.

5. A transparent solid detergent composition according to claim 1, wherein said composition is prepared by heating and dissolving said mixture of the fatty acid salts, the humectant and water, and pouring the mixture into a frame, cooling and solidifying.

6. A transparent solid detergent composition according to claim 1, wherein said polyether humectant includes from 2 to 100 moles of the addition-polymerized propylene oxide and up to 50 moles of the addition-polymerized ethylene oxide.

* * * * *